(12) United States Patent
Kuroda

(10) Patent No.: US 6,334,091 B1
(45) Date of Patent: Dec. 25, 2001

(54) APPARATUS AND METHOD FOR SENSING SOLUTE CONCENTRATION

(75) Inventor: Hajime Kuroda, Niigata (JP)

(73) Assignee: NEC Corporation, Tokyo (JP)

(*) Notice: Subject to any disclaimer, the term of this patent is extended or adjusted under 35 U.S.C. 154(b) by 0 days.

(21) Appl. No.: 09/190,061

(22) Filed: Nov. 12, 1998

(30) Foreign Application Priority Data

Nov. 12, 1997 (JP) .................................................. 9-310663

(51) Int. Cl.⁷ .............................. G01N 31/00; G06F 19/00
(52) U.S. Cl. ............................................... 702/23; 702/56
(58) Field of Search ........................ 702/56, 23; 364/560

(56) References Cited

U.S. PATENT DOCUMENTS 5,485,406 * 1/1996 Wanda et al. ..................... 364/560
6,026,348 * 2/2000 Hala ................................. 702/56

FOREIGN PATENT DOCUMENTS 60-135745   7/1985   (JP) .
7-55682     3/1995   (JP) .

* cited by examiner

*Primary Examiner*—John S. Hilten
*Assistant Examiner*—Charles H. Nolan, Jr.
(74) *Attorney, Agent, or Firm*—Foley & Lardner

(57) ABSTRACT

An apparatus includes a rotation member having a pair of floats having different weights. The floats are fixed thereto at such positions that turning moment is produced due to one of a floating force and a sinking force for each of the floats. The apparatus further includes a rotation angle sensor for sensing a change in rotation angle of the rotation member as a change in concentration of the solute in the solution.

21 Claims, 4 Drawing Sheets

APPARATUS AND METHOD FOR SENSING SOLUTE CONCENTRATION

BACKGROUND OF THE INVENTION

1. Field of the Invention

The present invention generally relates to a sensor for sensing concentrations of a solute in a solution and, in particular to method and apparatus for sensing concentrations of a solute in a solution such as a liquid ink or a liquid developer for use in a liquid developing electrostatic recording apparatus.

2. Description of the Related Art

There has been proposed a solute concentration detecting apparatus allowing automation of concentration adjustment in Japanese Patent Unexamined Publication No. 7-55682. More specifically, a solution reservoir is provided with a vertical passage through which two floats having different specific gravities are moving in a solution depending on the concentration of the solution. In the case of reduced concentration, one float having a smaller specific gravity is floating and the other having a greater specific gravity is sinking down As the concentration of the solute becomes higher, the other float having the greater specific gravity is floating and finally comes in contact with the one float having the smaller specific gravity. Therefore, when detecting the contact, it is determined that the concentration of the solution has reached the target concentration.

However, the above-mentioned concentration detecting apparatus can determine only whether the concentration of the solution has reached the target concentration. On other words, according to the conventional arrangement, only discrete concentration values are obtained. Therefore, precise concentration adjustment cannot be achieved.

Further, since the two floats are moving through the vertical passage, it is necessary to provide space for the vertical passage in the solution reservoir, resulting in increased size of the solution reservoir and reduced flexibility in design.

SUMMARY OF THE INVENTION

An object of the present invention is to provide solute concentration sensing method and apparatus that can sense the concentration of a solute with precision.

Another object of the present invention is to provide solute concentration sensing apparatus that can sense the concentration of a solute with reduced size and increased flexibility in design.

According to the present invention, two floats which are fixed to a rotation member and have different weights are placed within a reservoir storing the solution. A change in rotation angle of the rotation member is used as a change in concentration of the solution.

According to an aspect of the present invention, an apparatus includes a rotation member having a pair of floats fixed thereto at such positions that turning moment is produced due to one of a floating force and a sinking force for each of the floats, wherein the floats have different weights. The apparatus further includes a rotation angle sensor for sensing a change in rotation angle of the rotation member as a change in concentration of the solute in the solution.

According to another aspect of the present invention, an apparatus includes a rotation member having a pair of floats fixed thereto at such positions that turning moment is produced due to one of a floating force and a sinking force for each of the floats, wherein the floats have different weights and a rotation angle is sensor for sensing a change in rotation angle of the rotation member as a change in concentration of the solute in the solution, wherein a shaft of the rotation member is mechanically connected to a rotation axis of the rotation angle sensor. Further, the apparatus includes a casing containing the rotation member and having a plurality of openings formed so that the solution can flow through the openings, wherein the casing is fixed to the rotation angle sensor.

The rotation angle sensor may be fixed to a weight plate such that the rotation axis is perpendicular to the weight plate, the weight plate having a first portion and a second portion. The weight plate is rotatably connected at the first portion to an inner wall of the reservoir with a weight member fixed to the second portion thereof.

DETAILED DESCRIPTION OF THE PREFERRED EMBODIMENTS

Figure 1:
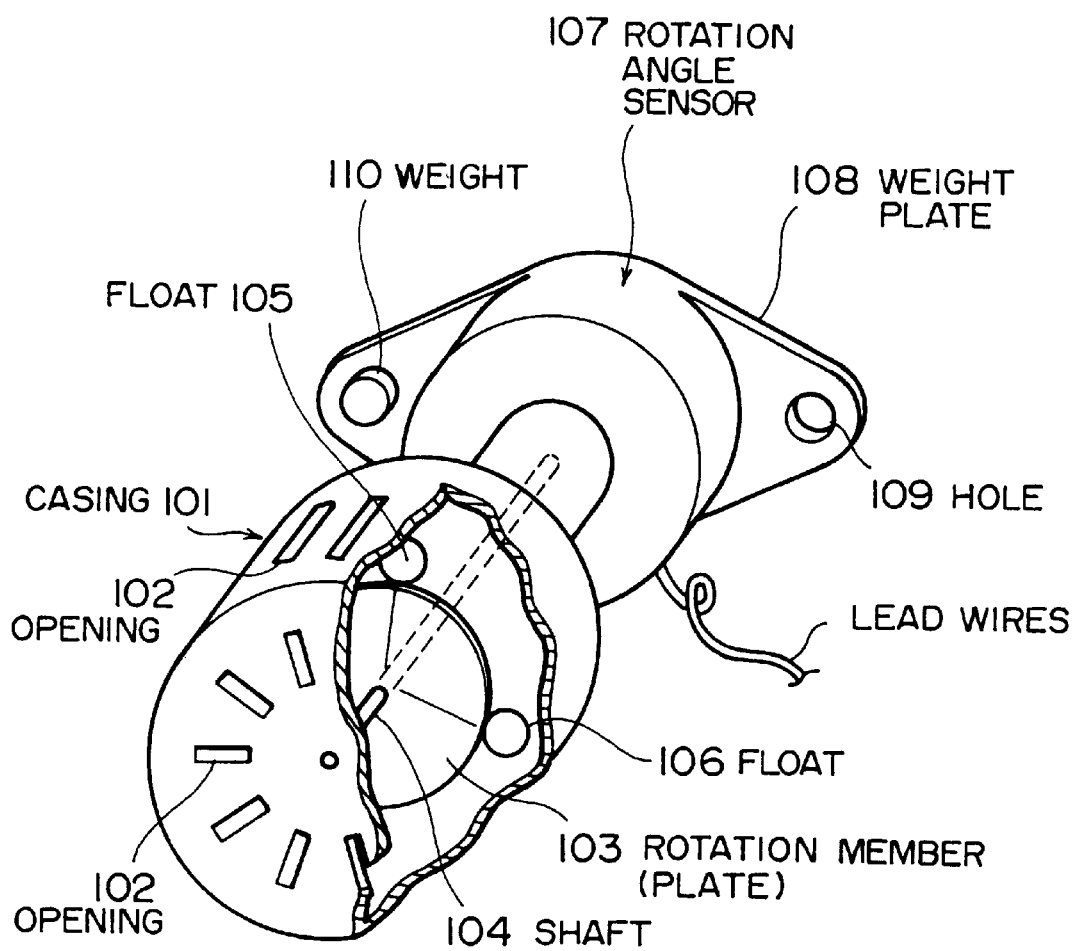
FIG. 1 a partially cutaway view in perspective of a sensor according to a first embodiment of the present invention.

Referring to FIG. 1, a solute concentration sensor according to a first embodiment of the present invention is composed of a casing 101 shaped like a cylinder having a plurality of openings 102 formed so that a solution can easily flow through them. Within the casing 101, a rotation member 103 (here, plate) is provided which is fixed to a shaft 104 so that the plate 103 rotate about an axis of the shaft 104.

The plate 103 is shaped like a disk and is made of material having a small specific gravity made uniform and further resisting solutions. For example, aluminum may be used. The plate 103 itself is shaped such that the turning moment is not produced. The plate 103 has a pair of floats 105 and 106 fixed to the edge thereof and they make an angle of 90 degrees. The floats 105 and 106 are preferably shaped such that resistance is reduced. In this embodiment, they are shaped like a sphere of cylinder and have the same volume but different specific gravities. Here the specific gravity of the float 105 is smaller than that of the float 106. The specific gravity of the solution will vary according to the solute concentration. Therefore, one of the floating force and sinking force, that is, the turning moment is produced depending on a difference in specific gravity between the solution and each of the floats 105 and 106. This causes the plate 103 having the floats 105 and 106 thereon to rotate depending on concentrations of the solution within the casing 101. The rotation is imparted to a rotation angle sensor 107 through the shaft 104.

The rotation angle sensor 107 may be a rotary encoder whose rotation axis is mechanically connected to the shaft 104. The rotation angle sensor 107 is fixed to a eight plate 108 that has a hole 109 formed at one end and has a weight 110 fixed thereto at the other and. The shape of the weight plate 108 is elongated in the direction of a line connecting the hole 109 and the weight 110. The weight plate 108 is made of material such as metal or resin, preferably stainless steel. The weight plate and the weight 110 are sufficiently heavy to such an extent that the buoyant forces of the floats 105 and 106 are negligible.

As will be described later, the hole 109 is used to rotatably connect the solute concentration sensor to the inner wall of a solution reservoir. In other words, the solute concentration sensor is suspended on the inner wall of the solution reservoir. Therefore, a straight line connecting the hole 109 and the weight 110 always extends in the direction of gravity even though the solution reservoir is not put in a horizontal position.

OPERATION

Figure 2C:
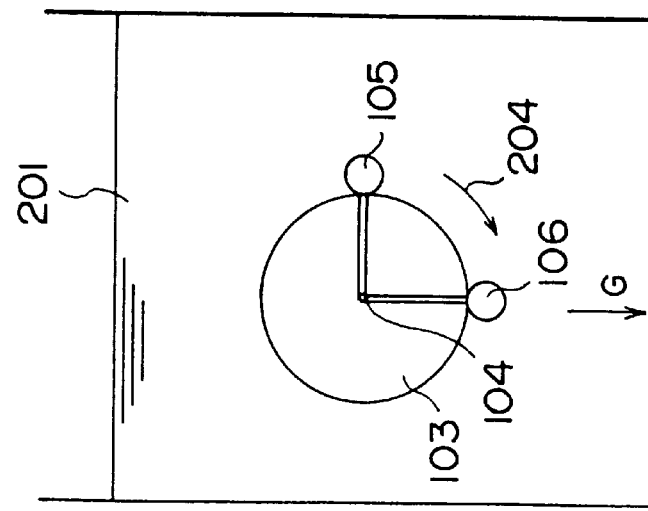
FIG. 2C is a diagram showing a state of the sensor of FIG. 1 when the solute concentration is relatively low.
Figure 2B:
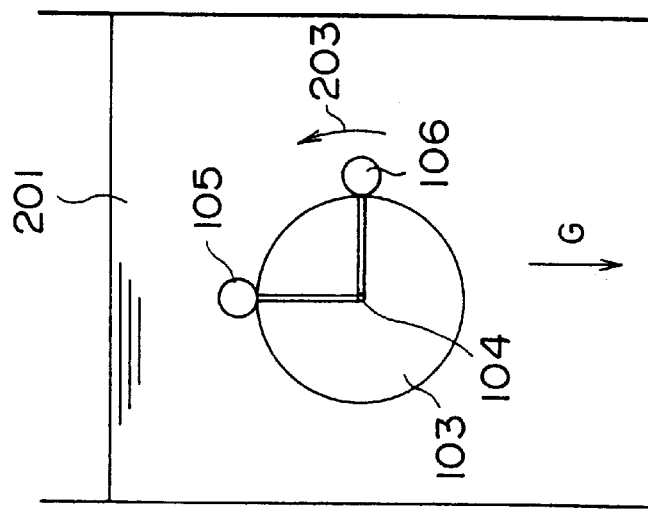
FIG. 2B is a diagram showing a state of the sensor of FIG. 1 when the solute concentration is relatively high.
Figure 2A:
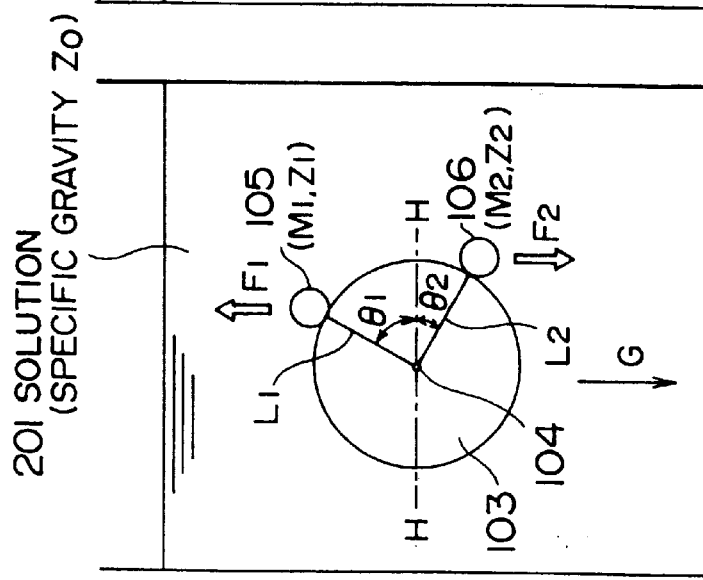
FIG. 2A is a diagram showing an operation of the sensor of FIG. 1.

Referring to FIG. 2A, a solution 201 is stored in a reservoir 202 and the solute concentration sensor sinks below the surface of the solution. It is assumed that the specific gravity of the solution 201 is $Z_0$, the volume and specific gravity of the float 105 are $M_1$ and $Z_1$, respectively, those of the float 106 are $M_2$ and $Z_2$, respectively, and the respective distances of the floats 105 and 106 from the shaft 104 are $L_1$ and $L_2$.

As described before, since the solute concentration sensor is suspended on the inner wall of the solution reservoir, a straight line connecting the bole 109 and the weight 110 always extends in the direction of gravity. Therefore, the horizontal line H—H normal to the direction G of gravity can be determined from the output of the rotation angle sensor 107.

In the case where the float 105 is located at a position making an angle $\theta_1$ from the horizontal line H—H and the float 106 is located at another position making an angle $\theta_2$ from the horizontal line H—H, the buoyant force $F_1$ of the float 105 is represented by $F_1=M_1(Z_0-Z_1)$ and, similarly the buoyant force $F_2$ of the float 106 is represented by $F_2=M_2(Z_0-Z_2)$. The plate 103 stops rotating when the floats 105 and 106 provide the same turning moment, that is, their positions satisfy the following equations:

$$F_1 \times L_1 \times \cos\theta_1 = F_2 \times L_2 \times \cos\theta_2.$$

Substitute $F_1=M_1(Z_0-Z_1)$, $F_2=M_2(Z_0-Z_2)$ and $\theta=\theta_1+\theta_2$ into the above equation, the following equation is obtained:

$$(Z_0-Z_1) \times M_1 \times L_1 \times \cos\theta_1 = (Z_0-Z_2) \times M_2 \times L_2 \times \cos(\theta-\theta_1) \quad (1).$$

Since the volume $M_1$, specific gravity $Z_1$ and distance $L_1$ of the float 105 and the volume $M_2$, specific gravity $Z_2$ and distance $L_2$ of the float 106 are given in advance, by measuring angle $\theta_1$, the specific gravity $Z_0$ can be calculated using the above equation (1). Alternatively, if the relationship between the specific gravity $Z_0$ and the angle $\theta_1$ is stored in a form of table, then the specific gravity $Z_0$ can be obtained from the table. Since the specific gravity $Z_0$ varies according to a concentration of the solution 201, the specific gravity $Z_0$ can be used as the concentration of the solution 201. After the plate 103 stops rotating, the angle $\theta_1$ is kept even if the reservoir 202 is tilted because the straight line connecting the hole 109 and the weight 110 is always parallel to the direction of gravity.

Referring to FIG. 2B, in the case where the specific gravity $Z_0$ of the solution 201 in relatively high, that is. $Z_0=Z_2$, the buoyant force $F_2$ becomes zero and the buoyant force $F_1$ becomes larger. Therefore, If the buoyant force $F_1$ is set to be sufficiently greater than the weight of the float 106 due to gravity, the plate 103 rotates in the direction of an arrow 203 and then stops rotating when the float 105 has reached the top position of the plate 103.

Referring to FIG. 2C, contrarily, in the case where the specific gravity $Z_0$ of the solution 201 is relatively low, that is, $Z_0=Z_1$, the buoyant force $F_1$ becomes zero and the buoyant force $F_2$ becomes negative, that is, the sinking force is applied to the float 106. Therefore, the plate 103 rotates in the direction of an arrow 204 and stops rotating when the float 106 has reached the bottom position of the plate 103.

EXAMPLES

In the case where the floats 105 and 106 have the same volume $M_1=M_2=5$ mm$^3$ and the same distance $L_1=L_2=10$ mm and further the positions of the floats 105 and 106 make an angle $\theta=90$ degrees, by substituting the above conditions into the equation (1), the following equation is obtained:

$$(Z_0-Z_1) \times \cos\theta_1 = (Z_0-Z_2) \times \cos(90-\theta_1).$$

Therefore, $$(Z_0 - Z_1)/(Z_0 - Z_2) = \cos(90 - \theta_1)/\cos\theta_1$$

$$= \sin\theta_1/\cos\theta_1$$

$$= \tan\theta_1.$$

Figure 3:
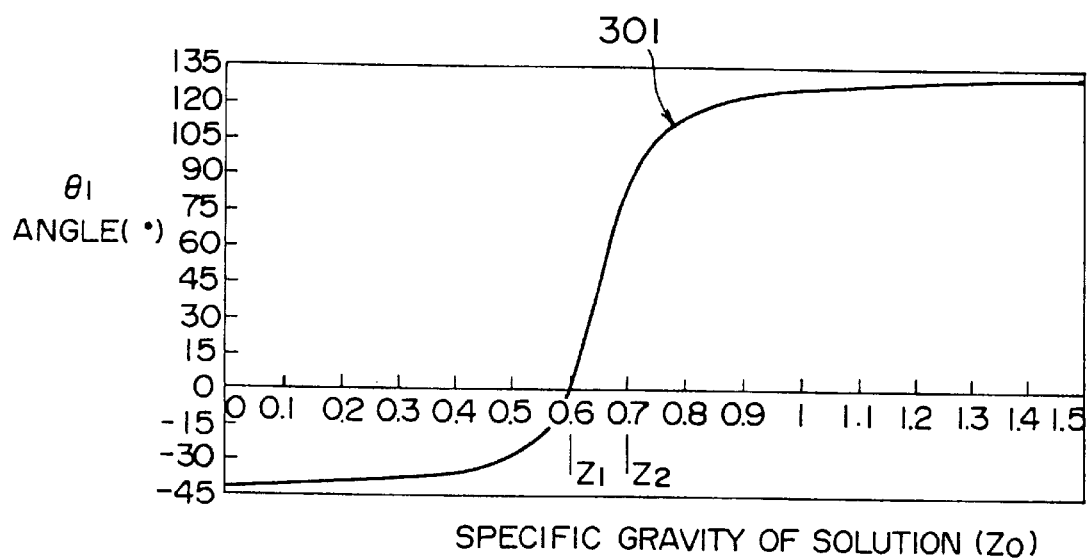
FIG. 3 is a graph showing an example of the rotation angle $\theta_1$ varying with specific gravity $Z_0$ of the solution.

Referring to FIG. 3, a curve 301 is obtained when $Z_1=0.6$ and $Z_2=0.7$. In the came where the specific gravities $Z_1$ and $Z_2$ are set within a relatively narrow range, a relatively high sensitive concentration sensor can be obtained. In this case as shown in FIG. 3, when the specific gravity $Z_0$ of the solution increases from 0.6 to 0.65, the plate 103 rotates about 45 degrees.

Figure 4:
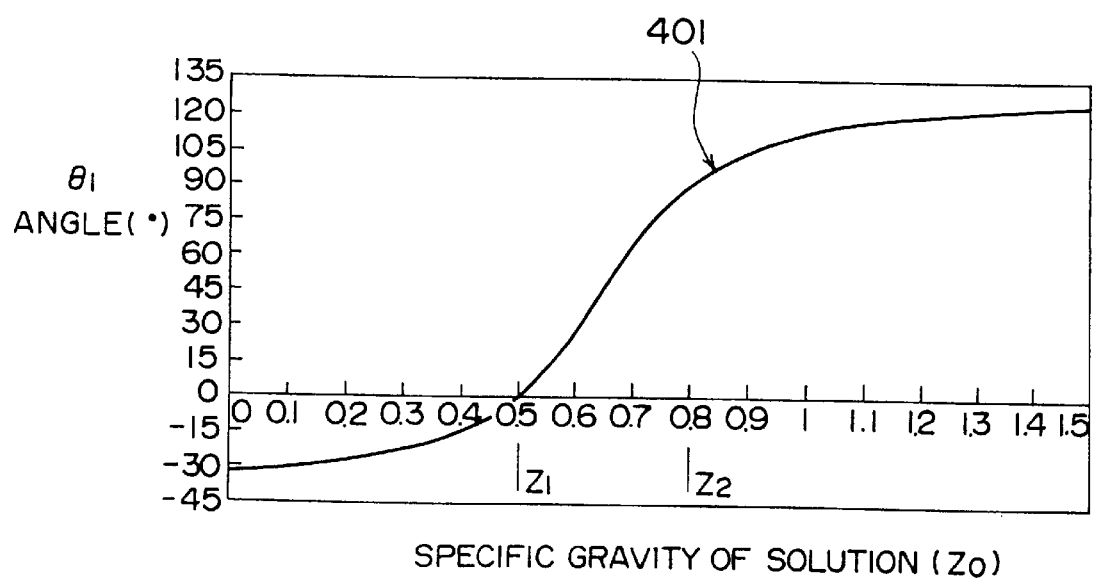
FIG. 4 is a graph showing another example of the rotation angle $\theta_1$ varying with specific gravity $Z_0$ of the solution.

Referring to FIG. 4, a curve 401 is obtained when $Z_1=0.5$ and $Z_2=0.8$. In the case where the specific gravities $Z_1$ and $Z_2$ are set with a relatively wide range, a relatively low sensitive concentration sensor can be obtained. In this case as shown in FIG. 4, when the specific gravity $Z_0$ of the solution increases from 0.6 to 0.65, the plate 103 rotates about 15 degrees only.

In this manner, by setting the respective specific gravities $Z_1$ and $Z_2$ to desired values included in an important range which needs precise concentration adjustment, precise concentration control can be achieved. The precision can be changed by selecting the specific gravities $Z_1$ and $Z_2$.

SECOND EMBODIMENT

The shape of the rotation member 103 is not limited to a disk as shown in FIG. 1. The rotation member 103 is preferably shaped such that the fluid resistance is reduced. For example, the rotation member 103 may be shaped like a sphere or a cylinder, Further, the floats 105 and 106 may be shaped like a sphere or a cylinder.

Figure 5:
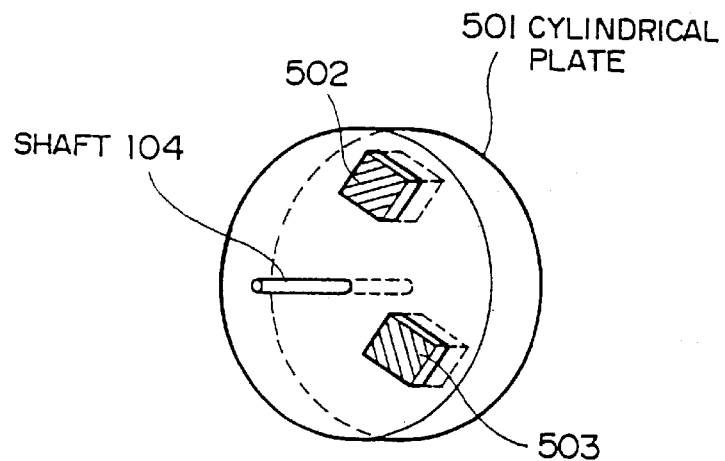
FIG. 5 is a perspective view showing a plate having floats embedded therein according to a second embodiment of the present invention.

Referring to FIG. 5, the rotation member 103 is a cylindrical plate 501 in which floats 502 and 503 having different weights are embedded at positions making a right angle. The cylindrical plate 501 may be made of resin or metal such as aluminum as described before. Since the floats 502 and 503 are embedded in the cylindrical plate 501, the cylindrical plate 501 can rotate with more reduced resistance. The protrusions of the flouts 502 and 503 are preferably dome-shaped to reduce in fluid resistance.

In the cases where the floats 502 and 503 are completely embedded in the cylindrical plate 501, further more reduced resistance is achieved.

CONTROL SYSTEM

Hereinafter, taking a liquid developer for use in a liquid developing electrostatic recording apparatus as an example, a toner concentration control system will be described The liquid developer is a solution of toner particulate and solvent.

Figure 6:
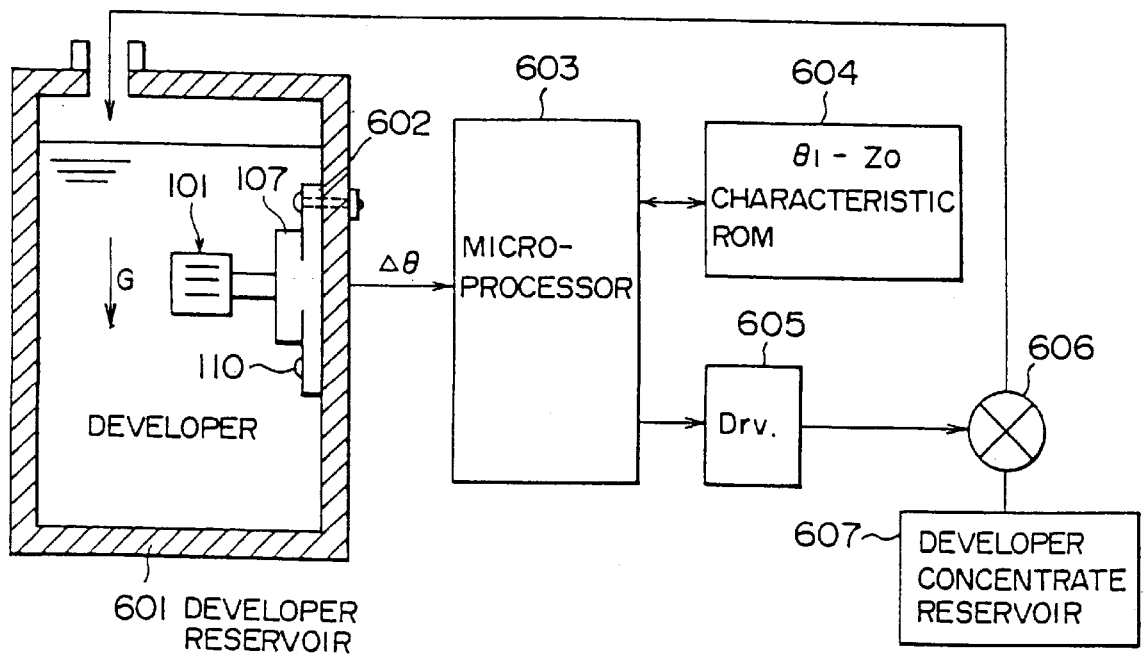
FIG. 6 is a block diagram showing a concentration control system using the sensor according to the present invention.

Referring to FIG. 6, the liquid developer is stored in a developer reservoir 601 in which a toner concentration sensor according to the present invention is suspended on the inner side wall 602 of the developer reservoir 601 with the one end of the weight plate 108 rotatably connected to the side wall 602 through the hole 109.

A microprocessor 603 is connected to a memory storing a predetermined specific gravity range corresponding to a desired toner concentration range and a read-only memory 604 storing characteristic data representing a $\theta_1$–$Z_0$ characteristic curve such as the curve 301 or 401 as shown in FIGS. 3 and 4. The microprocessor 603 receives an output signal from the rotary encoder 107 and calculates the angle $\theta_1$ of the float 105 with respect to the horizontal line H—H. Thereafter, the microprocessor 603 reads a specific gravity $Z_0$ corresponding to the calculated angle $\theta_1$ from the ROM 604 and compares the specific gravity $Z_0$ to the predetermined specific gravity range.

When the specific gravity $Z_0$ falls into the predetermined specific gravity range, it means that the toner concentration of the developer reservoir 601 falls into the desired toner concentration range. When the specific gravity $Z_0$ becomes lower than the lower limit of the predetermined Specific gravity range, it means that the toner concentration of the developer reservoir 601 is decreased and the microprocessor 603 controls a pump driver 605 so that a developer supplying pump 606 supplies developer concentrate from the developer concentrate reservoir 607 to the developer reservoir 601. This causes the toner concentration of the developer reservoir 601 to be increased. When the specific gravity $Z_0$ has fallen into the predetermined specific gravity range, the microprocessor 603 stops the pump 606 supplying the developer concentrate to the developer reservoir 601. In this way, the toner concentration of the developer reservoir 601 is kept substantially constants.

As described above, since a pair of floats having different specific gravities are fixed to a rotation member in predetermined positions, a change in solute concentration can be continuously sensed by measuring a change in rotation angle. Further, desired precision can be obtained by selecting the respective specific gravities of the floats. Especially, the precision can be increased in an important measurement range. Furthermore, since the sensor is suspended such that the sensor is always directed in parallel to the direction of gravity, the concentration sensing is not affected by a tilt of the solution reservoir.

What is claimed is:

1. An apparatus for sensing concentrations of a solute in a solution, comprising:
   a rotation member having a pair of floats fixed thereto at such positions that turning moment is produced due to one of a floating force and a sinking force for each of the floats, wherein the floats have different weights;
   a weight unit having a weight member adapted to extend in a direction of gravity when the apparatus is attached in a solution reservoir; and
   a rotation angle sensor for sensing a change in rotation angle of the rotation member as a change in concentration of the solute in the solution.

2. The apparatus according to claim 1, wherein the rotation member comprises:
   a rotation body which is freely rotatable about an axis and is shaped such that turning moment is not produced due to buoyant force,
   wherein the floats are a pair of protrusions fixed to the rotation body at the positions on the rotation body.

3. The apparatus according to claim 2, wherein the rotation body is shaped like one of a disk, a cylinder and a sphere.

4. The apparatus according to claim 2, wherein the protrusions are shaped like one of a sphere and a dome.

5. The apparatus according to claim 1, wherein the floats are fixed to the rotation member at the positions making an right angle with respect to a rotation center of the rotation member.

6. The apparatus according to claim 1, wherein the floats have the sam volume but different specific gravities.

7. The apparatus according to claim 2, wherein the protrusions have the same volume but different specific gravities.

8. An apparatus for sensing concentrations of a solute in a solution stored in a reservoir, comprising:
   a rotation member having a pair of floats fixed thereto at such positions that turning moment is produced due to one of a floating force and a sinking force for each of the floats, wherein the floats have different weights;
   a rotation angle sensor for sensing a change in rotation angle of the rotation member as a change in concentration of the solute in the solution, wherein a shaft of the rotation member is mechanically connected to a rotation axis of the rotation angle sensor; and
   a casing containing the rotation member and having a plurality of openings formed so that the solution can flow through the openings, wherein the casing is fixed to the rotation angle sensor.

9. The apparatus according to claim 8, wherein the casing is a cylindrical casing containing the rotation member such that the floats are freely rotatable.

10. The apparatus according to claim 8, wherein the rotation angle sensor is fixed to a weight plate such that the rotation axis is perpendicular to the weight plate, the weight plate having a first portion and a second portion, wherein the weight plate is rotatable connected at the first portion to an inner wall of the reservoir with a weight member fixed to the second portion thereof.

11. The apparatus according to claim 10, wherein the weight plate has a shape elongated in a direction of a line connecting the first and second portions and is suspended at the first portion thereof on the inner wall of the reservoir.

12. The apparatus according to claim 8, wherein the floats are fixed to the rotation member at the positions making an right angle with respect to a rotation center of the rotation member.

13. The apparatus according to claim 8, wherein the floats have the same volume but different specific gravities.

14. A method for sensing concentrations of a solute in a solution, comprising the steps of:
   placing a pair of floats fixed to a rotation member into the solution, wherein the floats having different weights and are fixed to the rotation member at such positions that turning moment is produced due to one of a floating force and a sinking force for each of the floats; and sensing a change in rotation angle of the rotation member to determine a change in concentration of the solute in the solution.

15. The method according to claim 14, wherein the floats are fixed to the rotation member at the positions making an right angle with respect to a rotation center of the rotation member.

16. The method according to claim 14, wherein the floats have the same volume but different specific gravities.

17. The apparatus according to claim 1, wherein the weight unit comprises a weight plate having a first portion and a second portion, wherein the weight plate is adapted to be rotatably connected at the first portion to an inner wall of the reservoir with the weight member fixed to the second portion of the weight plate.

18. A solution reservoir containing an apparatus for sensing concentration of a solute in a solution stored in the reservoir, comprising:
    the reservoir adapted to store the solution; and
    the apparatus adapted to sense concentration of the solute in the solution, the apparatus being attached to the reservoir, and the apparatus comprising:
        a rotation member having a pair of floats fixed thereto at such positions that turning moment is produced due to one of a floating force and a sinking force for each of the floats, wherein the floats have different weights;
        a rotation angle sensor for sensing a change in rotation angle of the rotation member as a change in concentration of the solute in the solution, wherein a shaft of the rotation member is mechanically connected to a rotation axis of the rotation angle sensor; and
        a casing containing the rotation member and having a plurality of openings formed so that the solution can flow through the openings, wherein the casing is fixed to the rotation angle sensor.

19. The reservoir according to claim 18, further comprising a weight plate, wherein the rotation angle sensor is fixed to the weight plate such that the rotation axis is perpendicular to the weight plate, the weight plate having a first portion and a second portion, wherein the weight plate is rotatably connected at the first portion to an inner wall of the reservoir with a weight member fixed to the second portion of the weight plate.

20. An apparatus for sensing concentrations of a solute in a solution, comprising:
    a rotation member having a pair of floats fixed thereto at such positions that turning moment is produced due to one of a floating force and a sinking force for each of the floats, wherein the floats have different weights and wherein the rotation member is shaped such that a turning moment is not produced due to buoyant force; and
    a rotation angle sensor for sensing a change in rotation angle of the rotation member as a change in concentration of the solute in the solution.

21. The apparatus according to claim 20, wherein the rotation member comprises a disk, a sphere, or a cylinder having a cylindrical axis parallel to the axis of rotation of the rotation member.

* * * * *